(12) United States Patent
Zhou et al.

(10) Patent No.: US 10,676,422 B2
(45) Date of Patent: Jun. 9, 2020

(54) KINETIC RESOLUTION OF RACEMIC HYDROXY ESTER VIA ASYMMETRIC CATALYTIC HYDROGENATION AND APPLICATION THEREOF

(71) Applicant: Zhejiang Jiuzhou Pharmaceutical Co., Ltd, Taizhou (CN)

(72) Inventors: Qilin Zhou, Tianjin (CN); Jianhua Xie, Tianjin (CN); Xiaohui Yang, Tianjin (CN); Lixin Wang, Tianjin (CN)

(73) Assignee: ZHEJIANG JIUZHOU PHARMACEUTICAL CO., LTD., Taizhou, Zhejiang (CN)

( * ) Notice: Subject to any disclaimer, the term of this patent is extended or adjusted under 35 U.S.C. 154(b) by 215 days.

(21) Appl. No.: 15/526,763

(22) PCT Filed: Aug. 8, 2015

(86) PCT No.: PCT/CN2015/086425
§ 371 (c)(1),
(2) Date: Feb. 24, 2019

(87) PCT Pub. No.: WO2016/082583
PCT Pub. Date: Jun. 2, 2016

(65) Prior Publication Data
US 2017/0334831 A1    Nov. 23, 2017

(30) Foreign Application Priority Data
Nov. 28, 2014  (CN) .......................... 2014 1 0714176

(51) Int. Cl.
| | |
|---|---|
| *C07C 69/675* | (2006.01) |
| *C07C 29/149* | (2006.01) |
| *C07C 31/20* | (2006.01) |
| *C07C 67/48* | (2006.01) |
| *B01J 31/18* | (2006.01) |
| *B01J 31/24* | (2006.01) |
| *C07B 53/00* | (2006.01) |
| *C07B 57/00* | (2006.01) |
| *C07D 211/02* | (2006.01) |
| *C07D 211/12* | (2006.01) |
| *C07D 305/06* | (2006.01) |
| *C07D 309/06* | (2006.01) |
| *C07D 473/06* | (2006.01) |
| *C07D 309/30* | (2006.01) |
| *C07C 69/732* | (2006.01) |
| *C07C 69/708* | (2006.01) |
| *C07C 33/26* | (2006.01) |

(52) U.S. Cl.
CPC .......... *C07C 69/675* (2013.01); *B01J 31/181* (2013.01); *B01J 31/189* (2013.01); *B01J 31/249* (2013.01); *C07B 53/00* (2013.01); *C07B 57/00* (2013.01); *C07C 29/149* (2013.01); *C07C 31/20* (2013.01); *C07C 67/48* (2013.01); *C07D 211/02* (2013.01); *C07D 211/12* (2013.01); *C07D 305/06* (2013.01); *C07D 309/06* (2013.01); *C07D 473/06* (2013.01); *B01J 31/24* (2013.01); *B01J 2231/646* (2013.01); *B01J 2531/827* (2013.01); *C07B 2200/07* (2013.01); *C07C 33/26* (2013.01); *C07C 69/708* (2013.01); *C07C 69/732* (2013.01); *C07D 309/30* (2013.01)

(58) Field of Classification Search
CPC ............ B01J 2231/646; B01J 2531/827; B01J 31/181; B01J 31/189; B01J 31/24; B01J 31/249; C07B 2200/07; C07B 53/00; C07B 57/00; C07C 29/149; C07C 31/20; C07C 33/26; C07C 67/48; C07C 69/675; C07C 69/708; C07C 69/732; C07D 211/02; C07D 211/12; C07D 305/06; C07D 309/06; C07D 309/30; C07D 473/06
See application file for complete search history.

(56) References Cited

U.S. PATENT DOCUMENTS 8,962,839 B2    2/2015    Zhou et al.

FOREIGN PATENT DOCUMENTS

CN    104355997 A    2/2015

OTHER PUBLICATIONS

Yang et al. (Catalytic Asymmetric Hydrogenation of d-Ketoesters: Highly Efficient Approach to Chiral 1,5-Diols, Asymmetric Catalysis, Angew. Chem. Int. Ed., 52, pp. 7833-7783, Published 2013) (Year: 2013).*
JAC vol. 136. No. 50 Year 2014 p. 17426-17429.
Angewandte Chemie International Edition vol. 50 No. 32 Year 2011 p. 7329-7332.

* cited by examiner

*Primary Examiner* — Yevgeny Valenrod
*Assistant Examiner* — Blaine G Doletski
(74) *Attorney, Agent, or Firm* — Liang Legal Group, PLLC

(57) ABSTRACT

The present invention relates to kinetic resolution of racemic δ-hydroxyl ester via asymmetric catalytic hydrogenation and an application thereof. In the presence of chiral spiro pyridyl phosphine ligand Iridium catalyst and base, racemic δ-hydroxyl esters were subjected to asymmetric catalytic hydrogenation to obtain extent optical purity chiral δ-hydroxyl esters and corresponding 1,5-diols. An optically active chiral δ-hydroxyl ester and 1,5-diols can be obtained at very high enantioselectivity and yield with relatively low usage of catalyst. The chiral δ-hydroxyl ester and 1,5-diols obtained by using the method can be used as a critical raw material for asymmetric synthesis of chiral drugs (R)-lisofylline and natural drugs (+)-civet, (−)-indolizidine 167B and (−)-coniine.

11 Claims, No Drawings

KINETIC RESOLUTION OF RACEMIC HYDROXY ESTER VIA ASYMMETRIC CATALYTIC HYDROGENATION AND APPLICATION THEREOF

The present application claims priority of Chinese application number 201410714176.3, filed to Chinese Patent Office on Nov. 28, 2014, titled "Kinetic resolution of racemic δ-hydroxy ester via asymmetric catalytic hydrogenation and application thereof", the entire contents of which are hereby incorporated by reference.

TECHNICAL FIELD

The present invention relates to a kenetic resolution method of racemic δ-hydroxy ester via asymmetric catalytic hydrogenation, the method can efficiently provide chiral δ-hydroxy esters and δ-1,5-diols in good yields with high enantioselectivities. The present invention also relates to there use in asymmetric synthesis of chiral drugs (R)-lisofylline and natural drugs (+)-civet, (−)-indolizidine 167B and (−)-coniine.

BACKGROUND

Optically active aliphatic alcohols are common substructures in natural products and are also useful chiral building blocks for the synthesis of chiral drugs. However, although in recent decades considerable attention has been devoted to the development of efficient methods for the synthesis of optically active aliphatic alcohols, including highly efficient asymmetric hydrogenation of aryl alkyl ketones to prepare optically active chiral alcohols, it still remains an open challenge for most of the methods are limited to synthesize the category of aryl alkyl type of optically active chiral alcohols. It still lacks of efficient method to prepare optically active aliphatic alcohols (de Vries, J. G.; Elsevier, C. J. *The Handbook of Homogeneous Hydrogenation*; Wiley-VCH: Weinheim, 2007; Zhao, B.; Han. Z.; Ding, K. *Angew. Chem., Int. Ed.* 2013, 52, 4744; Xie, J.-H.; Zhou, Q.-L. *Acta Chris. Sinica* 2012, 70, 1427). Catalytic asymmetric catalytic hydrogenation of aliphatic carbonyl compounds is an effective and atom economic, way to obtain chiral aliphatic alcohols, but this method is limited to the preparation of sterically hindered chiral aliphatic alcohols substituted with alkyl groups. For example, Noyori et al use chiral ruthenium diphosphine/amine pyridine catalysts in the catalytic hydrogenation of tert-butyl substituted di-alkyl alcohols with the enantioselectivity 98% ee (Ohkuma, T.; Sandoval, C. A.; Srinivasan, R; Lin, Q.; Vei, V Mufiiz, K. Noyori, R. J. *Am. Chem. Soc.* 2005, 127, 8288). While low enantioselectivity can be obtained in the catalytic hydrogenation of aliphatic ketones with little difference of the alkyl groups existed by the two sides of carbonyl groups.

Besides asymmetric catalytic hydrogenation method, using enzyme or chiral catalysts to resolve racemic alcohols has been studied to be a method to obtain active chiral alcohols, still, these methods are mainly used to prepare active chiral alcohols with the two alkyl groups which lied by two sides of hydroxyl existed big difference (Vedejs, E.; Jure, M. *Angew Chem. Int Ed.* 2005, 44, 3974; Pellissier, H. *Adv Synth. Catal.* 2011, 353, 1613.). In addition, the kinetic resolution method under developed was existed the problem that transferring one enantiomer to ketone or ester.

For this reason, to overcome the defects existed in preparing optically active aliphatic alcohols, we develop a highly efficient kinetic resolution of racemic δ-hydroxy ester via asymmetric catalytic hydrogenation of ester group. And this method has been efficiently obtained chiral δ-hydroxy esters and δ-1,5-diols in good yields with high enantioselectivities. It is the chiral spiro pyridylamidophosphine ligand complexed with Iridium to form the catalysts (Xie, J.-H.; Liu, X.-Y.; Xie, J.-B.; Wang, L.-X.; Zhou, Q.-L. *Angew. Chem., Int Ed.* 2011. 50, 7329; Zhou, Q.-L.; Xie, J.-H.; Liu, X.-Y.; Xie, J.-B.; Wang, L.-X. WO2012065571A1; Zhou, Q.-Xie, J.-H.; Liu, X.-Y.; Xie, J.-B.: Wang, L.-X. CN102040625 B) developed by us that realized the highly efficient kinetic resolution of racemic δ-hydroxy ester via asymmetric catalytic hydrogenation of ester group. Optically active chiral δ-hydroxy esters are obtained with the yield of 43-49 percent and with the enantioselectivity of 90-99 percent ee. Optically active chiral δ-1,5-diols are obtained with the yield of 44-50 percent and with the enantioselectivity of 91-97 percent ee. The kinetic resolution of asymmetric catalytic hydrogenation of ester group has high efficiency, and can obtain good results even reducing the amount of catalyst to 0.001 mol %. So the present kinetic resolution of racemic δ-hydroxy ester via asymmetric catalytic hydrogenation has the advantages of high efficiency, high enantioselectivity, economic, good operation, environmental friendly and can be used to industry manufacturing. The present kinetic resolution method of optically active aliphatic alcohols has been successfully used in asymmetric synthesis of chiral drugs (R)-lisofylline and natural drugs (+)-civet, (−)-indolizidine 167B and (−)-coniine via asymmetric catalytic hydrogenation.

SUMMARY OF THE INVENTION

The objective of the present invention is to provide a highly efficient kinetic resolution method of racemic δ-hydroxyl esters via asymmetric catalytic hydrogenation. In this way to provide an efficient method for preparing optical active chiral δ-hydroxyl esters and corresponding chiral 1,5-diols, which can further be used as the starting material in asymmetric synthesis of chiral drugs and natural products via asymmetric catalytic hydrogenation.

The kinetic resolution method disclosed in the present invention of racemic δ-hydroxyl esters via asymmetric catalytic hydrogenation, wherein, in the presence of chiral spiro pyridyl phosphine ligand Iridium catalyst and base, racemic δ-hydroxyl esters were subjected to asymmetric catalytic hydrogenation to obtain extent optical purity chiral δ-hydroxyl esters and corresponding 1,5-diols.

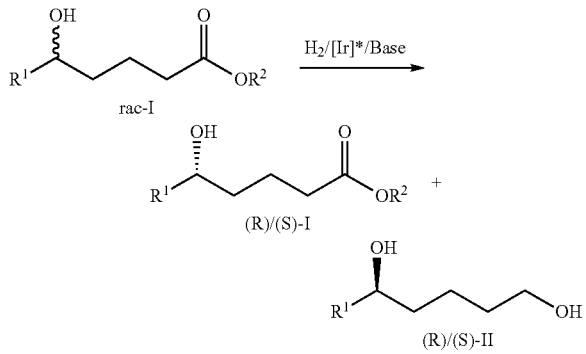

The obtained extent optical purity chiral δ-hydroxyl esters and corresponding 1,5-diols through the method disclosed in the present invention, which the configuration can be (R), or can be (S).

Further, when the obtained δ-hydroxyl esters is S configuration, the corresponding 1,5-diols is R configuration. When the obtained δ-hydroxyl esters is R configuration, the corresponding 1,5-diols is S configuration.

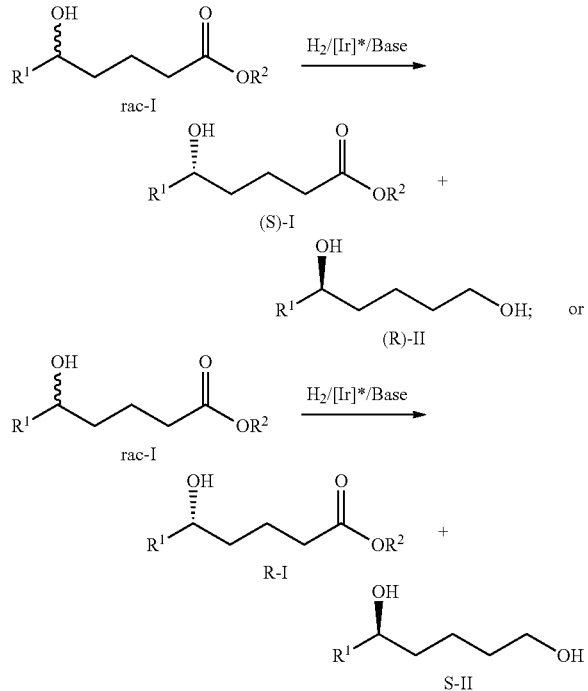

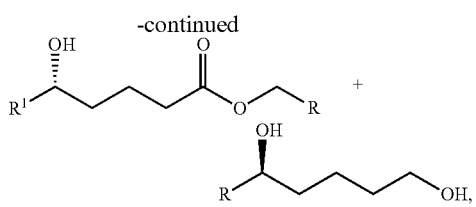

wherein, R is $C_1$~$C_8$ alkyl.

Preferably, the configuration of the chiral δ-hydroxyl esters is S, and the corresponding chiral 1,5-diols is R configuration.

The base used in the present kinetic resolution method of δ-hydroxyl esters and δ-hydroxyl lactone esters via asymmetric catalytic hydrogenation is alcohol alkalis, such as potassium tert-butoxide, sodium tert-butoxide, potassium isopropoxide or sodium isopropoxide; metal hydroxide, such as potassium hydroxide, sodium hydroxide, alkali carbonate, such as potassium carbonate or sodium carbonate. The preferable base is alcohol alkalis.

The preferable embodiment of the present kinetic resolution method of racemic δ-hydroxyl esters and δ-hydroxyl lactone esters via, asymmetric catalytic hydrogenation is carried out in the presence of solvent. The solvent used in the present kinetic resolution of δ-hydroxyl esters and δ-hydroxyl lactone esters via asymmetric catalytic hydrogenation is selected from any single or mixture of alcohol solvent, ether solvent or arene solvent. The alcohol solvent included methanol, ethanol, propanol, isopropanol, butanol. Ethers solvent included THF methyl tert-butyl ether or dioxane. Arene solvent included toluene, DMF or DMSO.

The specific embodiment of the present kinetic solution method of δ-hydroxyl esters and δ-hydroxyl lactone esters via asymmetric catalytic hydrogenation is, in the presence of organic solvent, were added δ-hydroxyl esters, catalysts, base. The reaction mixture was stirred for 0.5~24 h to react at the hydrogen atmosphere 1~100 atm to obtain optical active chiral δ-hydroxyl esters and corresponding chiral 1,5-diols.

But preferably the obtained δ-hydroxyl esters is S configuration, and the corresponding 1,5-diols is R configuration.

In the above general formula I and II, $R^1$ is $C_1$~$C_{20}$ alkyl, $C_1$~$C_{20}$ halogen alkyl, $C_2$~$C_{20}$ chain alkenyl, $C_4$~$C_{24}$ aryl, $C_5$~$C_{25}$ aryl alkyl, $C_6$~$C_{26}$ aryl alkenyl, —($C_1$~$C_8$ alkyl)-$OR^3$, —($C_1$~$C_8$ alkyl)-$SR^4$ or —($C_1$~$C_8$ alkyl)-$NR^5R^6$, wherein, $R^4$, $R^5$ and $R^6$ is separately $C_1$~$C_8$ alkyl, $C_5$~$C_{14}$ aryl alkyl or $C_4$~$C_{15}$ aryl, $R^5$ and $R^6$ also can be cyclic annular amino which have 4-20 carbon atoms.

$R^2$ is $C_1$~$C_5$ alkyl;

To be preferable, $R^1$ is $C_1$~$C_8$ alkyl, phenyl, cyclopentyl, tert-butyloxyl methyl; $R^2$ is ethyl.

What's more, racemic δ-hydroxyl esters also included δ-hydroxyl lactone esters, which is a side product in kinetic resolution method of δ-hydroxyl esters via asymmetric catalytic hydrogenation but can be further transferred in the reaction as a substrate.

Therefore, in another aspect, kinetic resolution method of δ-hydroxyl lactone esters via asymmetric catalytic hydrogenation was provided in the present invention, wherein, in the presence of chiral spiro pyridyl phosphine ligand catalyst and base, racemic δ-hydroxyl lactone esters, were subjected to asymmetric catalytic hydrogenation to obtain extent optical purity chiral δ-hydroxyl esters and corresponding 1,5-diols.

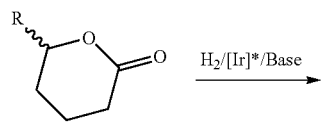

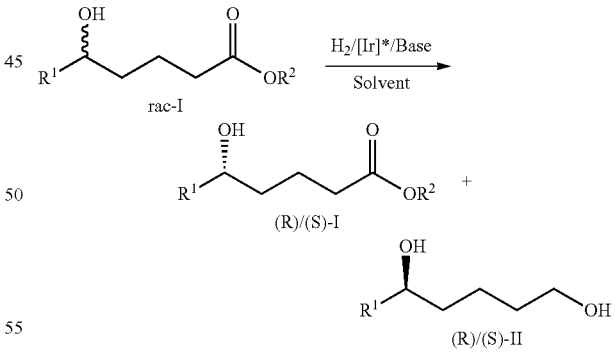

In the above general formula I and II.

$R^1$ is $C_1$~$C_{20}$ alkyl, $C_1$~$C_{20}$ halogen alkyl, $C_2$~$C_{20}$ chain alkenyl, $C_4$~$C_{24}$ aryl, $C_5$~$C_{25}$ aryl alkyl, $C_6$~$C_{26}$ aryl alkenyl, —($C_1$~$C_8$ alkyl)-$OR^3$, —($C_1$~$C_8$ alkyl)-$SR^4$ or —($C_1$~$C_8$ alkyl)-$NR^5R^6$, wherein, $R^4$, $R^5$ and $R^6$ is separately $C_1$~$C_8$ alkyl, $C_5$~$C_{14}$ aryl alkyl or $C_4$~$C_{15}$ alkyl, $R^5$ and $R^6$ also can be cyclic annular amino which have 4-20 carbon atoms.

$R^2$ is $C_1$~$C_5$ alkyl.

The configuration of the general formula alcohol I and II can be (R), or can be (S).

In the asymmetric catalytic hydrogenation reaction, the hydrogen pressure of asymmetric catalytic hydrogenation is 8-100 atm. To be preferable, the hydrogen pressure is 10 atm. The reaction temperature is 25-100° C. To be preferable, the reaction temperature is room temperature 25-30° C. The molar ratio of substrate racemic δ-hydroxyl esters and catalyst is 1000:1-100000:1. To be preferable, the molar ratio is 1000:1. The concentration of base is 0.01-0.1 M. To be preferable, the concentration of base is 0.02-0.06 M. The concentration of substrate is 0.001-2.0 M, the preferred substrate concentration is 0.01-1.0 M. The asymmetric catalytic hydrogenation reaction time is 1-121 h, and the preferred time is 0.5-6 h.

The present kinetic resolution method of racemic δ-hydroxy ester via asymmetric catalytic hydrogenation has been realized in the presence of chiral spiro pyridyl amido phosphine ligand Iridium complex catalyst with the following structure III (Xie, J.-H.; Liu, X.-Y.; Xie, J.-B.; Wang, L.-X.; Zhou, Q.-L. *Angew. Chem., int. Ed.* 2011, 50, 7329; Zhou, Q.-L.; Xie, Liu, X.-Y.; Xie, J.-B.; Wang, L.-X. WO2012065571A1; Zhou, Q.-L.; Xie, J.-H.; Liu, X.-Y.; Xie, J.-B.; Wang, L.-X. CN102040625 B),

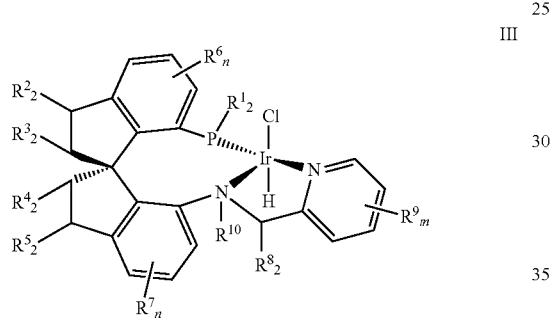

III the general structure formula III, wherein, $R^1$ is C1-C8 chain hydrocarbyl, phenyl, substituted phenyl, 1-napthyl, 2-naphthyl, heteroaryl or benzyl, and the substituent on said substituted phenyl is C1-C8 alkyl or alkoxy, with a substituent amount of 1-5, and said heteroaryl is furyl, thienyl or pyridyl;

$R^2$, $R^3$, $R^4$, $R^5$ are H, C1-C8 alkyl, phenyl, substituted phenyl, 1-naphthyl, 2-naphthyl, heteroaryl or benzyl, and the substituent on said substituted phenyl is C1-C8 hydrocarbyl, alkoxy, with a substituent amount of 1-5, and said heteroaryl is furyl, thienyl or pyridyl; or $R^2$-$R^3$, $R^4$-$R^5$ are incorporated into C3-C7 aliphatic ring, aromatic ring; $R^2$, $R^3$, $R^4$ and $R^5$ can be the same or different;

$R^6$, $R^7$ are selected from the group consisting of H, C1-C8 alkyl, C1-C8 alkoxy C1-C8 aliphatic amido group, n=0~3; or when n≥2, two adjacent $R^6$ groups or two adjacent $R^7$ groups can be incorporated into a C3-C7 aliphatic ring or aromatic ring, and $R^6$, $R^7$ can be the same or different;

$R^8$, $R^9$ are H, halogen, C1-C8 alkyl, C1-C8 alkoxy, phenyl, substituted phenyl, 1-naphthyl, 2-naphthyl, heteroaryl or benzyl, and the substituent on said substituted phenyl is halogen, C1-C8 alkyl, alkoxy, with a substituent amount of 1-5, and said heteroaryl is furyl, thienyl or pyridyl, and m=0-3; or when m≥2, adjacent $R^9$ or $R^3$ and $R^9$ groups can be incorporated into a C3-C7 aliphatic ring or aromatic ring, and $R^8$, $R^9$ can be the same or different;

$R^{10}$ is H, C1-C8 alkyl, phenyl, substituted phenyl, 1-naphthyl, 2-naphthyl, heteroaryl or benzyl, and the substituent on said substituted phenyl is C1-C8 alkyl, alkoxy, with a substituent amount of 1-5, and said heteroaryl is furyl, thienyl or pyridyl.

Preferable chiral spire pyridyl amido phosphine ligand Iridium complex catalyst included the following structure:

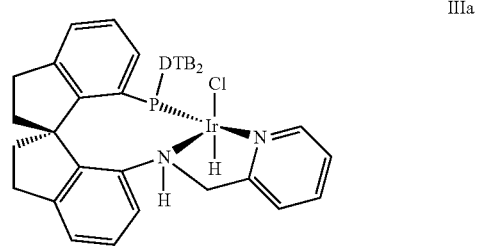

IIIa

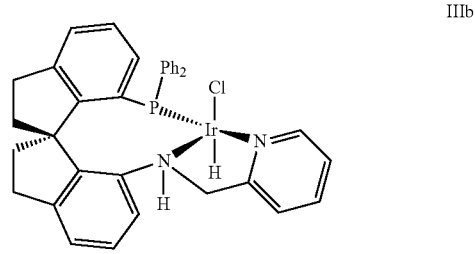

IIIb

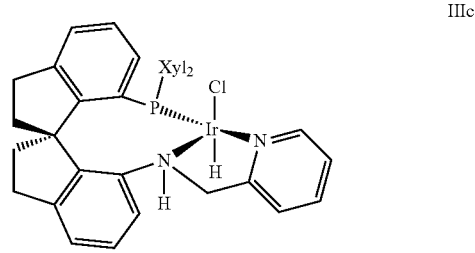

IIIc

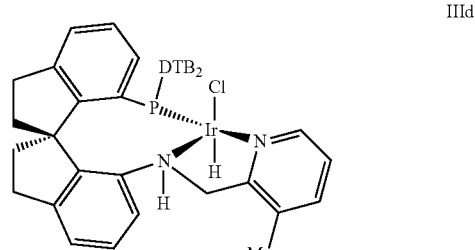

IIId

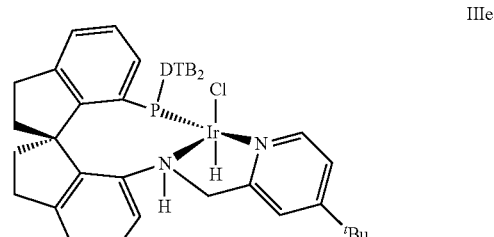

IIIe

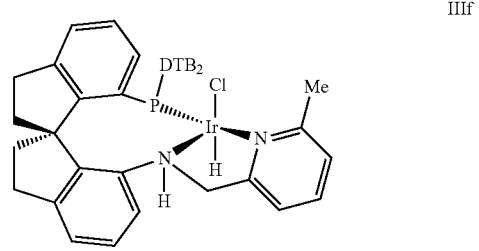

IIIf

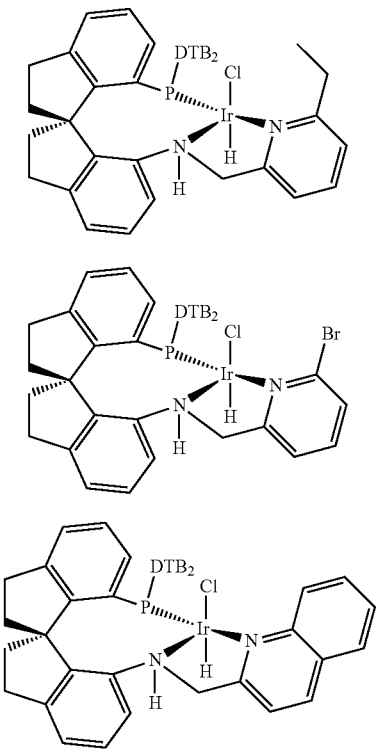

Wherein, DTB is 3,5-di-tert butyl phenyl, Xyl is 3,5-dimethyl phenyl, $^t$Bu is tert-butyl;

The Iridium catalysts with the structure can be R configuration or S configuration.

The present invention $C_1$~$C_{10}$ alkyl represents linear or branch chain which contains at most 10 carbon atoms, such as methyl, ethyl, n-propyl, isopropyl, cyclopropyl, n-butyl tert-butyl, pentyl, isoamyl, neopentyl, hexyl, tert-hexyl isoheptyl, n-octyl or isooctyl. $C_1$~$C_{10}$ alkoxy represents linked by oxygen atom with alkyl defined as above, such as methoxy, ethoxy, n-propoxy or n-butoxy etc. Aryl represents the substituents with aromatic ring structure property; such as phenyl, furyl, thienyl, pyridyl, quinolyl, indolyl, or aryl which the aromatic ring with different substituents in, such as p-methylphenyl, p-methoxy phenyl, p-chloro phenyl etc. Chain alkenyl represents chain alkyl which contains double bond, such as allyl, propenyl, 1-butenyl, 2-butenyl etc.

The chiral spiro pyridylamidophosphine ligand Itdidium catalysts used in the present invention for kinetic resolution of δ-hydroxyl esters via asymmetric catalytic hydrogenation, which are prepared as the method disclosed by the literature (Xie. J.-H.; Liu, X.-Y.; Xie, J.-B.; Wang, Zhou, Q.-L. *Angew. Int. Ed.* 2011, 50, 7329; Zhou Q.-L.; Xie, J.-H.; Liu. X.-Y.; Xie, J.-B.; Wang, L.-X. WO2012065571A1; Zhou, Q.-L.; Xie, J.-H.; Liu, X.-Y.; Xie, J.-B.; Wang, L.-X. CN102040625 B).

Under the pressure of 1~10 atm, at the temperature of 25~40° C., complexation reaction between 1~1.2 equivalent chiral spiro-pyridylamidophosphine compound with 1 equivalent Iridium metal precursor such as [Ir(cod)Cl]$_2$ (cod=cyclooctadiene [Ir(cod)$_2$]BF$_4$, [Ir(cod)$_2$]PF$_6$, [Ir(cod)$_2$]SbF$_6$, [Ir(cod)$_2$]OTf) is performed in an organic solvent for 0.5-4 hours, then desolventization is performed to obtain the corresponding Iridum catalysts.

The preferable Iridium catalyst precursor is [Ir(cod)Cl]$_2$, the preferable ligand is (R)—N-(3-methylpyridyl-2-methyl)-7-di-(3,5-di-tert-butyl phenyl)phosphine-7'-amino-1,1'-spiro-di-hydroge n indene.

The provided optical, chiral δ-hydroxy ester and δ-1,5-diols in the present invention can be the chiral starting material, which are used in asymmetric synthesis of chiral drugs (R)-lisotylline and natural drugs (+)-civet, (−)-indolizidine 167B and (−)coniine via asymmetric catalytic hydrogenation.

The present invention has the advantages shown as follows: the kinetic resolution of asymmetric catalytic hydrogenation of ester group has high efficiency, high enantioselectivity, economic, good operation, environmental friendly and can be used to industry manufacturing. The present method can obtain high yield and enantioselectivity optical active compounds which is very important compounds in chiral drugs and natural products via asymmetric catalytic hydrogenation, even reducing the amount of catalyst to very low amount. So the present kinetic resolution of racemic δ-hydroxy ester via asymmetric catalytic hydrogenation has the advantages of high efficiency. The present kinetic resolution method of optically active aliphatic alcohols has been successfully used in asymmetric synthesis of chiral drugs (R)-lisofylline and natural drugs (+) civet, (−)-indolizidine 167B and (−)-coniine via asymmetric catalytic hydrogenation.

DETAILED EMBODIMENTS

In order to further understand the present invention, preferred embodiments of the present invention will be described by reference to the examples, but it should be appreciated that these descriptions are merely intended to further illustrate the features and advantages of the present invention, rather than limiting the claims of the invention.

Example 1

Preparation of Chiral Spino Pyridyl Amide Phosphine Ligand Iridium Catalyst, Use Iridium Catalyst IIId as the Example Under the atmosphere of 1 atm hydrogen, [Ir(cod)Cl]$_2$ (30 mg, 0.045 mmol) and (R)—N-(3-methylpyridyl-2-methyl)-7-di-(3,5-di-tert-butyl phenyl)phosphine-7'-amino-1,1'-spiro-di-hydrogen indene (70.5 mg, 0.094 mmol) were dissolved in ethanol (6 mL), the reaction mixture was stirred at room temperature for 3 hours, then desolventization at reduced pressure is performed to obtain light yellow solid. The solid is directly used in hydrogenation reaction.

Other Iridium catalyst can be prepared as the same method as above.

Example 2

Kinetic Resolution of Racemic δ-hydroxy Esters via Catalytic Ester Hydrogenation Under the protection of nitrogen, to a hydrogenation vessel in an autoclave was added 1 mmol 5-hydroxyl ethyl hexanoate, 0.001 mmol catalyst in ethanol solution (0.5 mL), a solution of t-BuOK in EtOH (0.04 mmol) and 1 mL ethanol. After sealing, the autoclave was purged with hydrogen by pressurizing to 10 atm. The reaction mixture was stirred at room temperature for 0.5-6 hour. After the hydrogenation reaction finished, slowly releasing hydrogen, the solvent was subjected to desolventization at reduced pressure. Using NMR to measure transformation, HPLC to measure the enantioselectivity of the compound, the result is shown as table 1.

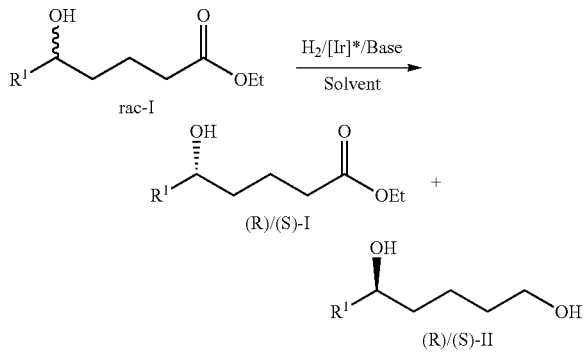

TABLE 1

|  |  |  | (R)/(S)-I |  | (R)/(S)-II |  |
|---|---|---|---|---|---|---|
| entry | R | time (h) | conv (%) | yield (%) | ee (%) | yield (%) | ee (%) |
| 1 | Me | 1 | 50 | 47 | 93.7 | 46 | 94.2 |
| 2 | Et | 2 | 52 | 44 | 95.3 | 47 | 94.4 |
| 3 | $^n$Pr | 2 | 52 | 43 | 95.8 | 47 | 96.0 |
| 4 | $^n$Bu | 2 | 50 | 45 | 95.1 | 48 | 95.9 |
| 5 | $^i$Bu | 3 | 48 | 49 | 89.7 | 44 | 95.9 |
| 6 | $^i$Pr | 6 | 53 | 43 | 97.5 | 49 | 96.6 |
| 7 | Cy | 5 | 54 | 44 | 99.0 | 50 | 93.5 |
| 8 | MeO(CH$_2$)$_3$ | 1 | 50 | 45 | 97.2 | 46 | 91.2 |
| 9 | Me$_2$CHCH(CH$_2$)$_2$ | 2 | 53 | 44 | 93.5 | 48 | 92.5 |
| 10 | Ph | 0.5 | 49 | 49 | 93.7 | 47 | 94.8 |

Example 3

High Transformation Experiment (S/C=100000) of Kinetic Resolution of Racemic δ-hydroxy Esters via Catalytic Ester Hydrogenation Under the protection of nitrogen, to a hydrogenation vessel in an autoclave was added 50 mmol 5-hydroxyl ethyl hexanoate, 0.0005 mmol catalyst in ethanol solution (1 mL), a solution of t-BuOK (1.8 mmol) in EtOH (9 mL) and 9 mL ethanol. After sealing, the autoclave was purged with hydrogen by pressurizing to 17 atm. The reaction mixture was stirred at room temperature for 24 hours. After the hydrogenation reaction finished, slowly releasing hydrogen, the solvent was subjected to desolventization at reduced pressure. Using NMR to measure the transformation with 52%, using HPLC to measure ee value of (S)-1 compound with 97% and ee value of (R)-II compound with 93% enantioselectivity.

Example 4

Asymmetric Synthesis of (+)-civet 4.1 Synthesis of (S)-5-methyl-5-valerolactone

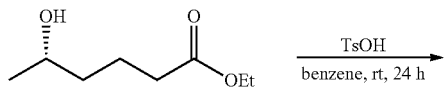

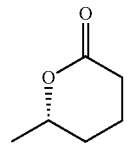

To a solution of (S)-5-methyl-5-valerolactone (528 mg, 3 mmol) benzene (10 mL) was added TsOH (114 mg, 0.6 mmol) at room temperature. After the reaction mixture was stirred for 24 h, saturated NaHCO$_3$ was added. The layers were separated and the aqueous layer was extracted with EtOAc. The combined organic layers were washed with brine, dried over MgSO$_4$ and concentrated in vacuo to afford a crude product, which was purified by chromatography on silica gel column (petroleum ether/ethyl acetate=3:1) to provide the desired product (S)-4 (308 g, 90% yield) as a colorless oil.

[α]$^{20}_D$ –31.1 (c 1.0, EtOH). $^1$H NMR (400 MHz, CDCl$_3$) δ 4.48-4.37 (m, 1H), 2.64-2.51 (m, 1H), 2.50-2.37 (m, 1H), 1.99-1.77 (m, 3H), 1.60-1.43 (m, 1H), 1.36 (d, J=6.4 Hz, 3H).

4.2 Synthesis of (S)-6-hydroxyl-2-octadienoic Acid Ethyl Ester

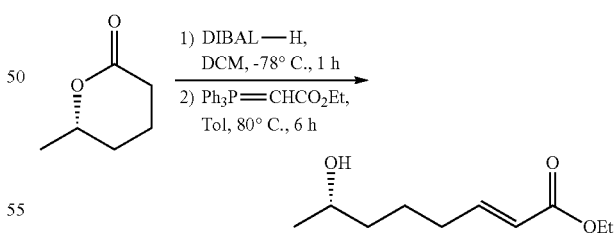

Under the protection of nitrogen, to a solution of (S)-5-methyl-5-valerolactone (228 g, 2 mmol) in DCM (5 mL) was added dropwise DIBAL-H (1.0 M in hexane, 2 mL, 2 mmol) at −78° C. After finishing adding, the reaction mixture was stirred for 1 h at this temperature, saturated sodium potassium tartrate was added. The mixture was allowed to warm to roof temperature and vigorously stirred for 1 h. The layers were separated and the aqueous layer was extracted with DCM. The combined organic layers were washed with brine, dried over MgSO$_4$ and concentrated in vacuo to afford colorless liquid. The liquid is directly used into the next step without further purifying. To a solution of the liquid as above in Tol (10 mL) was added (carbethoxymethylene)-triphenylphosphorane (1.04 g, 3 mmol), and the mixture was stirred at 80° C. for 6 h. The solvent was evaporated and the remaining crude product was purified by chromatography on silica gel column (petroleum ether/ethyl acetate=3:1) to provide the desired product (308 mg, 83% yield over two steps) as a colorless oil.

$[\alpha]^{20}{}_D$+9.1 (c 1.0, CHCl$_3$). $^1$H NMR (400 MHz, CDCl$_3$) δ 6.95 (dt, J=15.6, 6.8 Hz 1H), 5.81 (dt, J=15.6, 1.6 Hz, 1H), 4.17 (q, J=7.2 Hz, 2H), 3.85-3.74 (m, 1H), 2.26-2.17 (m, 2H), 1.66-1.39 (m, 5H), 1.27 (t, J=7.2 Hz, 3H), 1.18 (d, J=6.4 Hz, 3H). $^{13}$C NMR (100 MHz, CDCl$_3$) δ 166.69, 148.87, 121.51, 67.74, 60.16, 38.54, 32.02, 24.15, 23.54, 14.22. HRMS (ESI) Calcd for C$_{10}$H$_{18}$O$_3$ ([M+H]$^+$): 187.1329, Found: 187.1327.

4.3 Synthesis of (+)-civet

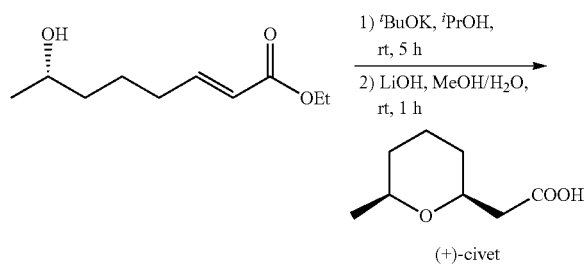

To (S)-δ-hydroxyl-2-octadienoic acid ethyl ester obtained from step 4.2, were added $^i$PrOH (5 mL) and $^t$BuOK (22.4 mg, 0.2 mmol), the mixture were stirred at room temperature for 5h. The solvent of the reaction mixture was slowly removed under reduce pressure and the residue was dissolved with methanol (5 mL). 1 N LiOH (5 mL. 5 mmol) was added to the mixture and the reaction mixture was stirred for 1 h. After acidified with 2 N HCl to pH 1, the solution was extracted with EtOAc, dried over anhydrous MgSO$_4$, and concentrated in vacuo to yield a crude product, which was purified by flash chromatography on silica gel column (petroleum ether/ethyl acetate=1:1) to provide the desired product (+)-civet (107 mg, 68% yield over two steps as a colorless oil.

$[\alpha]^{20}{}_D$+22.0 (c 1.0, CHCl$_3$). $^1$H NMR (400 MHz, CDCl$_3$) δ 9.40 (s, 1H), 3.81-3.71 (m, 1H), 3.56-3.45 (m, 1H), 2.56 (dd, J=15.6, 7.6 Hz, 1H), 2.46 (dd, J=15.6, 5.2 Hz, 1H), 1.86-1.77 (m, 1H), 1.67-1.46 (m, 3H), 1.30-1.19 (m, 2H), 1.16 (d, J=6.4 Hz, 3H). $^{13}$C NMR (100 MHz, CDCl$_3$) δ 175.72, 74.41, 73.93, 41.23, 32.71, 30.72, 23.16, 21.94.

Example 5

Synthesis of (−)-indolizidine 167B 5.1 Protection of Hydroxyl Group

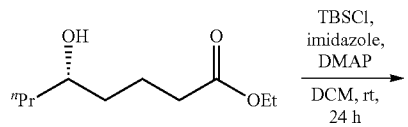

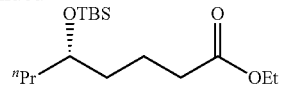

To a solution of (S)-5-hydroxyl octadienoic acid ethyl ester (1.76 g, 9.4 mmol) in DCM (40 mL) was added imidazole (959 mg, 14.1 mmol), DMAP (115 mg, 0.94 mmol) and TBSCl (1.7 g, 11.3 mmol). The reaction mixture was stirred at room temperature for 24 h. Then the reaction mixture was quenched with saturated NH$_4$Cl. The layers were, separated and the aqueous layer was extracted with DCM. After dried over anhydrous MgSO$_4$ and concentrated in vacuo to afford a crude product, which was purified by flash chromatography on silica gel column petroleum ether/ethyl acetate=80:1) to provide the desired product (2.61 g, 92% yield) as a colorless oil.

$[\alpha]^{20}{}_D$−0.4 (c 4.7, CHCl$_3$). $^1$H NMR (400 MHz, CDCl$_3$) δ 4.12 (q, J=7.2 Hz 2H), 3.69-3.61 (m, 1H), 2.29, (t, J=7.2 Hz, 2H), 1.75-1.55 (m, 2H), 1.50-1.28 (m, 6H), 1.25 (t, J=7.2 Hz, 3H), 0.91-0.85 (m, 12H), 0.03 (s, 6H), $^{13}$C NMR (100 MHz, CDCl$_3$) δ 173.70, 71.67, 60.15, 39.29, 36.38, 34.50, 25.88, 20.81, 18.47, 18.09, 14.28, 14.22, −4.48, −4.51. HRMS (ESI) Calcd for C$_{16}$H$_{35}$O$_3$Si ([M+H]$^+$): 303.2350, Found: 303.2354.

5.2 Establish of Amide Functional Group

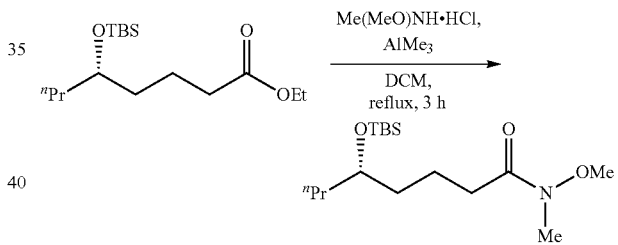

Under the N$_2$ atmosphere, to a solution of N,O-dimethyl hydroxylamine hydrochloric acid salt (2.52 g, 25.8 mmol) in DCM (70 mL), was slowly added AlMe$_3$. (25.8 mL, 1.0 M in hexane, 2.58 mmol), the reaction mixture was stirred for 0.5 h at room temperature. Then (S)-5-hydroxyl ethyl caprylate which the hydroxyl group was protected with TBS obtained from 5.1 in DMC was added, the reaction mixture was reacted when heated to reflux for 3 h and cooled to room temperature. Then the reaction mixture was quenched with 0.5 N HCl. The layers were separated and the aqueous layer was extracted with DCM. After dried over anhydrous MgSO$_4$ and concentrated in vacuo to afford a crude product, which was purified by flash chromatography on silica gel column (petroleum ether/ethyl acetate=1:2) to provide the desired product (2.55 g, 93% yield) as a colorless oil.

$[\alpha]^{20}{}_D$−3.4 (c 1.0, CHCl$_3$). $^1$H NMR (400 MHz, CDCl$_3$) δ 3.70-3.63 (m, 4H), 3.17 (s, 3H), 2.41, (t, J=8.0 Hz, 2H), 1.74-1.59 (m, 2H), 1.51-1.23 (m, 6H), 0.93-0.84 (m, 12H), 0.04 (d, J=1.2 Hz, 6H). $^{13}$C NMR (100 MHz, CDCl$_3$) δ 174.59, 71.89, 61.15, 39.25, 36.73, 32.09, 25.89, 20.45, 18.48, 18.09, 14.29, −4.46, −4.50. HRMS (ESI) Calcd for C$_{16}$H$_{36}$NO$_3$Si ([M+H]$^+$): 318.2459, Found: 318.2465.

5.3 Synthesis of Acetal or Ketal

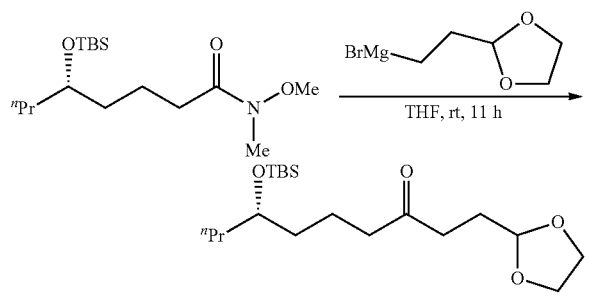

Under the N₂ atmosphere, to a solution of amide compound (2.55 g, 8.0 mmol) obtained from 5.2 in THF (60 mL) was added grignard reagent (24 mL, 1.0 M in THF, 24.0 mmol), the solution was reacted for 11 h at the room temperature. Then the reaction mixture was quenched with saturated NH₄Cl. The layers were separated and the aqueous layer was extracted with EtOAc. After dried over anhydrous MgSO₄ and concentrated in vacuo to afford a crude product, which was purified by flash chromatography on silica gel column (petroleum ether/ethyl acetate=15:1) to provide the desired product (2.76 g, 96% yield) as a colorless oil.

$[\alpha]^{20}_D$ -0.8 (c 1.0, CHCl₃). ¹H NMR (400 MHz, CDCl₃) δ 4.89 (t, J=4.4 Hz 1H), 3.98-3.78 (m, 4H), 3.67-3.58 (m, 1H), 2.51 (t, J=7.2 Hz, 2H), 2.40 (t, J=7.2 Hz, 2H), 2.00-1.92 (m, 2H), 1.69-1.49 (m, 2H), 1.44-1.22 (m, 6H), 0.91-0.83 (m, 12H), 0.02 (s, 6H). ¹³C NMR (100 MHz, CDCl₃) δ 210.03, 103.32, 71.81, 64.93, 42.94, 39.26, 36.48, 36.36, 27.54, 25.88, 19.66, 18.46, 18.09, 14.28, -4.48. HRMS (ESI) Calcd for $C_{19}H_{39}O_4Si$ ([M+H]⁺): 359.2612, Found: 359.2616.

5.4 Deprotection of Protecting Group

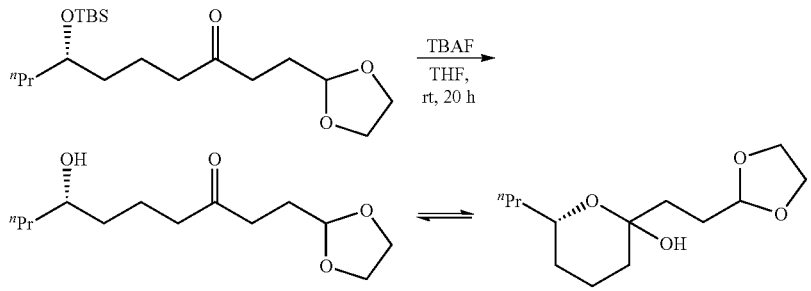

To a solution of acetal or ketal compound (2.76 g, 7.7 mmol) obtained from 5.3 in THF (20 mL) was added TBAF (38.5 mL, 1.0 M in THF 38.5 mmol), the solution was reacted for 20 h at the room temperature. Then the reaction mixture was quenched with saturated NH₄Cl. The layers were separated and the aqueous layer was extracted with EtOAc. After dried over anhydrous MgSO4 and concentrated in vacuo to afford a crude product, which was purified by flash chromatography on silica gel column (petroleum ether/ethyl acetate=3:1) to provide the desired product (1.54 g). The desired product is the mixture of δ-hydroxyl ketone and hemiketal with the yield 82%.

¹H NMR (400 MHz, CDCl₃) δ 4.93-4.81 (m, 1H), 4.01-3.89 (m, 2H), 3.88-3.78 (m, 2.3H), 3.59-3.49 (m, 0.7H), 3.32 (s, 0.2H), 2.51 (t, J=Hz, 1.4H), 2.44 (t, J=7.2 Hz, 1.4H), 1.99-1.90 (m, 1.7H), 1.86-1.51 (m, 4H), 1.48-1.22 (m, 6H) 0.95-0.81 (m, 3H). ¹³C NMR (100 MHz, CDCl₃) δ 210.24, 104.29, 103.24, 95.44, 71.04, 69.32, 64.89, 42.46, 39.56, 38.40, 36.73, 36.46, 36.36, 34.00, 31.15, 27.49, 26.49, 26.64, 19.62, 19.16, 18.76, 18.63, 14.04.

5.5 Synthesis of Compound Containing —N₃ Group

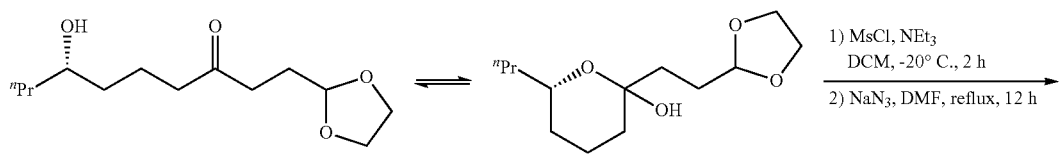

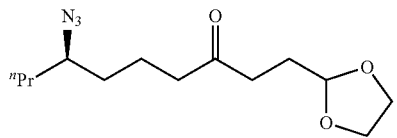

To a solution of the compound (635 mg, 2.6 mmol) obtained from 5.4 in DCM (20 mL), were added Et$_3$N (394 mg, 3.9 mmol) and MeSO$_3$Cl (388 mg, 3.4 mmol), the reaction mixture was reacted for 3 h. Then the reaction mixture was quenched with saturated NH$_4$Cl. The layers were separated and the aqueous layer was extracted with EtOAc. After dried over anhydrous MgSO4 and concentrated in vacuo to afford a crude product as a colorless liquid. DMF (20 mL) was added for attenuation, then NaN$_3$ (3.38 g, 5.2 mmol) was added in batches. The solution was stirred for 20 h to react at the temperature of 100° C. Then the reaction mixture was cooed to room temperature, and subjected to filter to remove NaN$_3$. The organic layer was washed with H$_2$O, dried over anhydrous MgSO4 and concentrated in vacuo to afford a crude product, which was purified by flash chromatography on silica gel column (petroleum ether/ethyl acetate=10:1) to provide the desired product as a colorless liquid (420 mg, yield 60%).

$[\alpha]^{20}_D$-2.8 (c 1.0, CHCl$_3$). $^1$H NMR (400 MHz, CDCl$_3$) δ 4.86 (t, J=4.4 Hz 1H), 3.95-3.74 (m, 4H), 3.25-3.14 (m, 1H), 2.48 (t, J=7.2 Hz, 2H), 2.41 (t, J=7.2 Hz, 2H), 2.41 (t, J=7.2 Hz, 2H), 1.97-1.88 (m, 2H), 1.75-1.53 (m, 2H), 1.52-1.26 (m, 6H), 0.88 (t, J=7.2 Hz, 3H). $^{13}$C NMR (100 MHz, CDCl$_3$) δ 209.34, 103.11, 64.82, 62.45, 42.01, 36.31, 36.24, 33.57, 27.41, 20.15, 19.14, 13.71. HRMS (ESI) Calcd for C$_{13}$H$_{23}$N$_3$O$_3$Na ([M+Na]$^+$): 292.1632, Found: 292.1636.

5.6 Synthesis of (−)-Indolizidine 167B

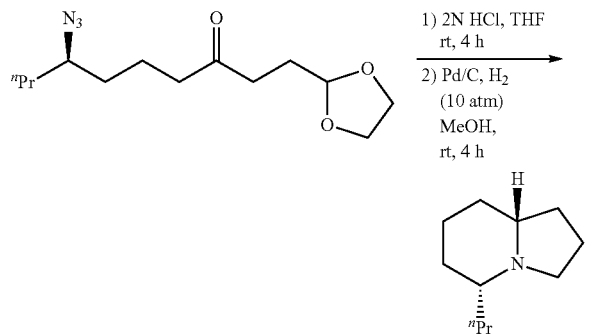

To a solution of the compound (250 mg, 0.93 mmol) obtained from 5.5 in THF (9 mL) was added 2 N HCl solution and reacted for 4 h at the room temperature. the solution was extracted with EtOAc. The solution was dried over anhydrous MgSO$_4$ and concentrated in vacuo to afford a crude product, which was purified by flash chromatography on silica gel column (petroleum ether/ethyl acetate=5:1) to provide the desired product as a colorless liquid (186 mg, 89% yield).

$[\alpha]^{20}_D$-6.6 (c 2.0, CHCl$_3$). $^1$H NMR (400 MHz, CDCl$_3$) δ 9.80 (s, 1H), 3.32-3.20 (m, 1H), 2.80-2.69 (m, 4H), 2.52 (t, J=7.2 Hz, 2H), 1.83-1.59 (m, 2H), 1.54-1.35 (m, 6H), 0.93 (t, J=7.2 Hz, 3H). $^{13}$C NMR (100 MHz, CDCl$_3$) δ 208.10, 200.40, 62.52, 42.11, 37.44, 36.35, 34.56, 33.60, 20.24, 19.25, 13.81.

To the hydrogenation reaction vessel were added the above colorless liquid (50 mg, 0.22 mmol), 10 wt % Pd/C (23 mg, 0.022 mmol), and MeOH (5 mL), the reaction mixture was stirred for 4 h to react after injecting the hydrogen to 10 atm. The reaction mixture was filtrated, dissolved to obtain a colorless liquid. EtOAc was added to attenuation, then the liquid was acidized with 1 N HCl (5 mL), the liquid was layered. The water layer was washed with EtOAc and saturated NaHCO$_3$ was added to adjust the pH to be alkalescence. The water layer was extracted by EtOAc, dried and concentrated to obtain a colorless liquid (26 mg, yield 71%).

$[\alpha]^{20}_D$-101.3 (c 1.0, CH$_2$Cl$_2$), $^1$H NMR (400 MHz, CDCl$_3$) δ 3.26 (dt, J=2.0, 8.8 Hz, 1H). 1.96 (q, J=8.8 Hz, 1H), 1.87-1.57 (m, 8H), 1.49-1.09 (m, 8H), 0.90 (t, J=7.2 Hz, 3H). $^{13}$C NMR (100 MHz, CDCl$_3$) δ 64.97, 63.67, 51.53, 36.89, 31.00, 30.82, 30.52, 24.67, 20.37, 19.08, 14.50. HRMS (ESI) Calcd for C$_{11}$H$_{22}$N ([M+H]$^+$): 168.1747, Found: 168.1750.

Example 6

Synthesis of (R)-lisofylline 6.1 Selectivity Protection of Hydroxyl

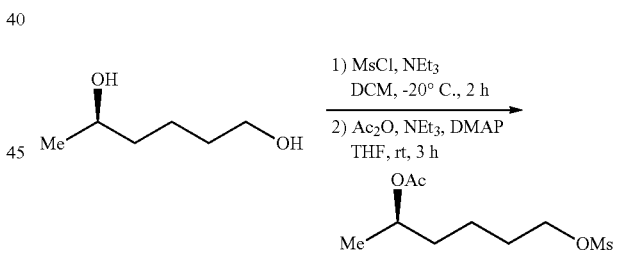

To a solution of (R)-hexane-1,5-diol (730 mg, 5 mmol) in DCM (10 mL) was added Et$_3$N (555 mg 5.5 mmol) and MsCl (570 mg, 5 mmol) at −20° C. under N$_2$ atmosphere. The reaction mixture was stirred at the same temperature for 2 h and quenched with saturated NH$_4$Cl. The layers were separated and the aqueous layer was extracted with DCM. The combined extracts were washed with saturated NaHCO$_3$ and brine, dried over anhydrous MgSO$_4$ and concentrated in vacuo to afford a crude product, which was purified by flash chromatography on silica gel column (petroleum ether/ethyl acetate=3:1) to provide the desired product (R)-5-hydroxyhexyl methanesulfonate (672 mg, 69% yield) as a colorless oil.

$[\alpha]^{20}_D$-9.6 (c 1.0, CHCl$_3$). $^1$H NMR (400 MHz, CDCl$_3$) δ 4.24 (t, J=6.4 Hz, 2H), 3.87-3.77 (m, 1H), 3.01 (s, 3H), 1.83-1.73 (m, 2H), 1.68 (s, 1H), 1.58-1.42 (m, 4H), 1.20 (d, J=6.0 Hz, 3H). $^{13}$C NMR (100 MHz, CDCl$_3$) δ 69.92, 67.63, 38.37, 37.31, 29.03, 23.56, 21.64. HRMS (ESI) Calcd for $C_7H_{17}O_4S$ ([M+H]$^+$): 197.0843, Found: 197.0841.

A mixture of (R)-5-hydroxyhexyl methanesulfonate (390 mg, 1.74 mmol), Ac$_2$O (673 mg, 6.6 mmol), NEt$_3$ (707 mg, 7.0 mmol), DHAP (61 it 0.5 mmol) and THF (10 mL) were stirred at room temperature for 4 h. After removing of THF in vacuo, the residue was diluted with EtOAc (10 mL). The solution was washed with saturated NaHCO$_3$, dried over anhydrous MgSO$_4$ and concentrated in vacuo to afford a crude product, which was purified by flash chromatography on silica gel colunm (petroleum ether/ethyl acetate=3:1) to provide the desired product (426 mg, 92% yield) as a colorless oil.

$[\alpha]^{20}{}_D$–1.0 (c 1.0, CHCl$_3$). $^1$H NMR (400 MHz, CDCl$_3$) δ 4.94-4.83 (m, 1H), 4.21 (t, J=6.4 Hz, 2H), 3.00 (s, 3H), 2.02 (s, 3H), 1.81-1.70 (m, 2H), 1.66-1.39 (m, 4H), 1.20 (d, J=6.4 Hz, 3H). $^{13}$C NMR (100 MHz, CDCl$_3$) δ 170.71, 70.39, 69.67, 37.32, 35.15, 28.85, 21.33, 21.31, 19.87. HRMS (ESI) Calcd for $C_9H_{19}O_5S$ ([M+H]$^+$): 239.0948, Found: 239.0950.

6.2 Synthesis of (R)-Lisofylline

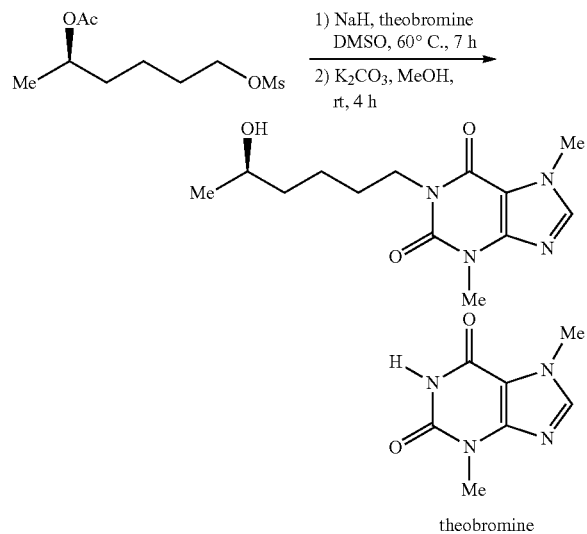

To a solution of NaH (38.4 mg, 1.6 mmol) in DMSO (10 mL) was slowly added the theobromine (288 mg, 1.6 mmol) under N$_2$ atmosphere. The reaction mixture was heated to 60° C. and added slowly a solution of compound obtained in 6.1 (288 mg, 1.6 mmol) in DMSO (2 mL). After stirring 7 h and cooling to room temperature, H$_2$O was added to the reaction mixture. The solution was extracted with EtOAc, and the combined extracts were washed with brine, dried over anhydrous MgSO$_4$ and concentrated in vacuo to afford a crude white product. The obtained crude white product was dissolved in MeOH (20 mL) and K$_2$CO$_3$ (1.1 g, 8 mmol) was added to the solution at room temperature. After stirring 4 h, H$_2$O was added to the reaction mixture. The solution was extracted with EtOAc, and the combined extracts were washed with brine, dried over anhydrous MgSO$_4$ and concentrated in vacuo to afford a crude product, which was purified by flash chromatography on silica gel colunm with ethyl acetate as the eluent to provide the desired white product (R)-lisofylline (375 mg, 77% yield) as white solid. m.p.123-125° C.

$[\alpha]^{20}{}_D$–5.0 (c 1.0, CHCl$_3$). $^1$H NMR (400 MHz, CDCl$_3$) δ 7.50 (s, 1H), 4.00 (t, J=7.6 Hz, 2H), 3.97 (s, 3H), 3.83-3.75 (m, 1H), 3.55 (s, 3H), 1.73-1.62 (m, 2H), 1.56-1.35 (m, 5H), 1.17 (d, J=6.0 Hz, 3H). $^{13}$C NMR (100 MHz, CDCl$_3$) δ 155.33, 151.47, 148.71, 141.39, 107.64, 67.79, 41.10, 38.73, 33.55, 29.66, 27.86, 23.46, 22.87. HRMS (ESI) Calcd for $C_{13}H_{21}N_4O_3$ ([M+H]$^+$): 281.1609, Found: 281.1613.

Example 7

Synthesis of (–)-Coniine 7.1 Synthesis of Piperidyl Compound

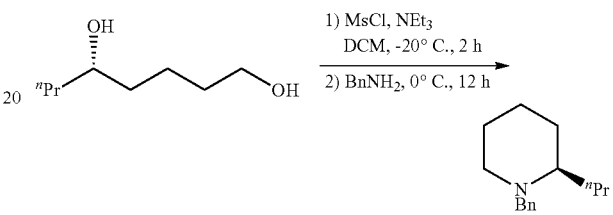

To a solution of (5)-octane-1,5-diol (231 mg, 1.58 mmol) in DCM (10 mL) was added NEt$_3$ (479 mg, 4.74 mmol) and MeSO$_3$H (450 mg, 3.95 mmol) at the temperature of –20° C. and reacted for 2 h at the temperature. The reaction mixture was subjected to cancellation with saturated NH$_4$Cl solution and then was extracted by DCM. The solution was washed with saturated NaHCO$_3$, dried over anhydrous MgSO$_4$ and concentrated in vacuo to afford a colorless liquid. Benzylamine was added to the colorless liquid at the temperature of 0° C. and stirred for 12 h to react. The reaction mixture was concentrated to get out of benzylamine at reduced pressure. The solution was extracted with EtOAc, and the combined extracts were washed with saturated NaHCO$_3$, dried over anhydrous MgSO$_4$ and concentrated in vacuo to afford a crude product, which was purified by flash chromatography on silica gel column (petroleum ether/ethyl acetate=15:1) to provide the desired product as a colorless liquid (236 mg, 69% yield).

$[\alpha]^{20}{}_D$–77.6 (c 2.0, CHCl$_3$). $^1$H NMR (400 MHz, CDCl$_3$) δ 7.35-7.27 (m, 4H), 7.25-7.19 (m, 1H), 3.97 (d, J=13.2 Hz, 1H), 3.22 (d, J=13.2 Hz, 1H), 2.73 (dt, H=11.2, 4.4 Hz, 1H), 2.32-2.23 (m, 1H), 2.07-1.97 (m, 1H), 1.71-1.23 (m, 10H), 0.91 (t, J=7.2 Hz, 3H). $^{13}$C NMR (100 MHz, CDCl$_3$) δ 139.84, 128.93, 128.05, 126.55, 60.61, 57.50, 51.68, 34.10, 30.25, 25.14, 23.71, 18.69, 14.63.

7.2 Synthesis of (–)-Coniine

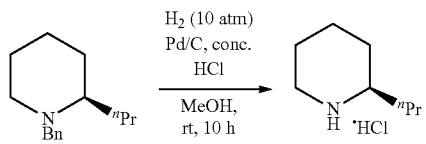

To the hydrogenation reaction vessel were added piperidyl compound obtained in 7.1 (17 mg, 0.078 mmol), 10 wt. % Pd/C (8.3 mg, 0.0078 mmol.) concentrated HCl (0.1 mL) and MeOH (3 mL), the reaction mixture was stirred for 3 h to react after injecting the hydrogen to 10 atm. The reaction mixture was filtrated, dissolved to obtain light yellow solid (13 mg, 98% yield). m.p. 220-222° C.

$[\alpha]^{20}_D$-6.4 (c 1.0, EtOH). $^1$H NMR (400 MHz, CDCl$_3$) δ 9.23 (br s, 1H), 8.95 (br s, 1H), 3.62-3.43 (m, 1H), 3.05-2.75 (m, 2H), 2.10-1.58 (m, 7H), 1.58-1.35 (m, 3H), 0.95 (t, J=6.0 Hz, 3H). $^{13}$C NMR (100 MHz, CDCl$_3$) δ 57.23, 45.07, 35.41, 28.10, 22.39, 22.23, 18.64, 13.77.

The invention claimed is:

1. A method for kinetic resolution of racemic δ-hydroxyl esters via asymmetric catalytic hydrogenation, comprising: in the presence of a chiral Spiro pyridyl phosphine ligand Iridium catalyst and a base, subjecting racemic δ-hydroxyl esters to asymmetric catalytic hydrogenation to obtain a chiral δ-hydroxyl ester and a corresponding 1,5-diols,

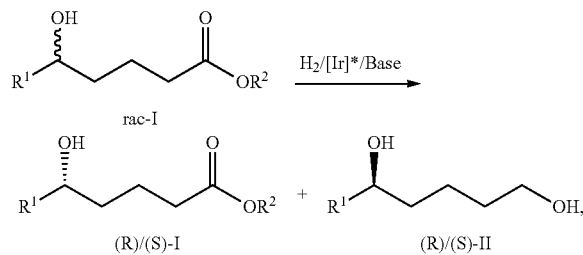

wherein when the produced δ-hydroxyl ester is in an S configuration, the corresponding 1,5-diols is in an R configuration; or wherein when the produced δ-hydroxyl ester is in an R configuration, the corresponding 1,5-diols is in an S configuration;

wherein $R^1$ is $C_1$-$C_{20}$ alkyl, $C_1$-$C_{20}$ halogen alkyl, $C_2$-$C_{20}$ chain alkenyl, $C_4$-$C_{24}$ aryl, $C_5$-$C_{25}$ aryl alkyl, $C_6$-$C_{26}$ aryl alkenyl, $C_1$-$C_8$ alkyl)-OR$^3$, —($C_1$-$C_8$ alkyl)-SR$^4$ or —($C_1$-$C_8$ alkyl)-NR$^5$R$^6$, wherein R$^4$, R$^5$, and R$^6$ are independently $C_1$-$C_8$ alkyl, $C_5$-$C_{14}$ aryl alkyl, or $C_4$-$C_{15}$ aryl, or alternatively, R$^5$ and R$^6$, together with the N atom to which they attach, form a cyclic amino group having 4-20 carbon atoms; and $R^2$ is $C_1$-$C_5$ alkyl and wherein the chiral spiro pyridyl phosphine ligand Iridium catalyst has a structure of formula III,

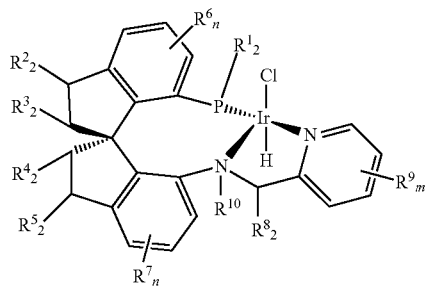

wherein R$^1$ is C1-C8 chain hydrocarbyl, phenyl, substituted phenyl, 1-naphthyl, 2-naphthyl, heteroaryl, or benzyl, and wherein a substituent on said substituted phenyl is C1-C8 alkyl or alkoxy, with a substituent number of 1-5, and said heteroaryl is furyl, thienyl, or pyridyl;

R$^2$, R$^3$, R$^4$, and R$^5$ are independently H, C1-C8 alkyl, phenyl, substituted phenyl, 1-naphthyl, 2-naphthyl, heteroaryl, or benzyl, and wherein a substituent on said substituted phenyl is C1-C8 hydrocarbyl or alkoxy, with a substituent number of 1-5, and said heteroaryl is furyl, thienyl, or pyridyl; or R$^2$-R$^3$, R$^4$-R$^5$ are incorporated into a C3-C7 aliphatic ring or an aromatic ring; wherein R$^2$, R$^3$, R$^4$, and R$^5$ are the same or different;

R$^6$ and R$^7$ are independently selected from the group consisting of H, C1-C8 alkyl, C1-C8 alkoxy, and C1-C8 aliphatic amido group, n=0-3; or when n≥2, two adjacent R$^6$ groups or two adjacent R$^7$ groups are incorporated into a C3-C7 aliphatic ring or an aromatic ring, and wherein R$^6$ and R$^7$ are the same or different;

R$^8$ and R$^9$ are independently H, halogen, C1-C8 alkyl, C1-C8 alkoxy, phenyl, substituted phenyl, 1-naphthyl, 2-naphthyl, heteroaryl, or benzyl, and wherein a substituent on said substituted phenyl is halogen, C1-C8 alkyl, alkoxy, with a substituent number of 1-5, and said heteroaryl is furyl, thienyl, or pyridyl, and m=0-3; or when m≥2, adjacent R$^9$ groups, or R$^8$ and R$^9$ groups, are incorporated into a C3-C7 aliphatic ring or an aromatic ring, and wherein R$^8$ and R$^9$ are the same or different; and R$^{10}$ is H, C1-C8 alkyl, phenyl, substituted phenyl, 1-naphthyl, 2-naphthyl, heteroaryl, or benzyl, and wherein a substituent on said substituted phenyl is C1-C8 alkyl or alkoxy, with a substituent number of 1-5, and said heteroaryl is furyl, thienyl, or pyridyl.

2. The method for kinetic resolution of racemic δ-hydroxyl esters via asymmetric catalytic hydrogenation according to claim 1, comprising the following hydrogenation process in a solvent:

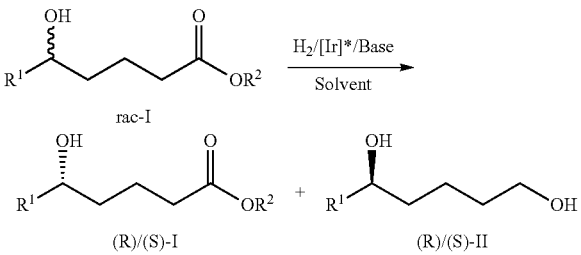

wherein R$^1$ and R$^2$ are as defined in claim 1.

3. The method for kinetic resolution of racemic δ-hydroxyl esters via asymmetric catalytic hydrogenation according to claim 1, wherein R$^1$ is $C_1$-$C_8$ alkyl, phenyl, cyclopentyl, or tert-butyloxyl methyl.

4. The method for kinetic resolution of racemic δ-hydroxyl esters via asymmetric catalytic hydrogenation according to claim 1, wherein, in which the chiral spiro pyridyl amido phosphine ligand Iridium catalyst has a structure of formula III,

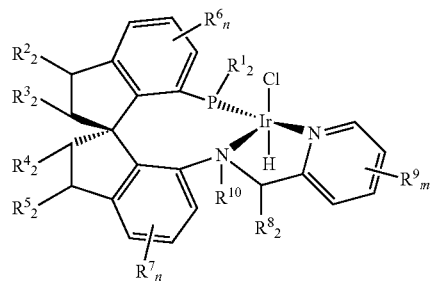

wherein R¹ is $C_1$-$C_8$ chain hydrocarbyl, phenyl, substituted phenyl, 1-naphthyl, 2-naphthyl, heteroaryl, or benzyl, and wherein a substituent on said substituted phenyl is C1-C8 alkyl or alkoxy, with a substituent number of 1-5, and said heteroaryl is furyl, thienyl, or pyridyl;

R², R³, R⁴, and R⁵ are independently H, C1-C8 alkyl, phenyl, substituted phenyl, 1-naphthyl, 2-naphthyl, heteroaryl, or benzyl, and wherein a substituent on said substituted phenyl is C1-C8 hydrocarbyl or alkoxy, with a substituent number of 1-5, and said heteroaryl is furyl, thienyl, or pyridyl; or R²-R³, R⁴-R⁵ are incorporated into a C3-C7 aliphatic ring or an aromatic ring; wherein R², R³, R⁴, and R⁵ are the same or different;

R⁶ and R⁷ are independently selected from the group consisting of H, C1-C8 alkyl, C1-C8 alkoxy, and C1-C8 aliphatic amido group, n=0-3; or when n≥2, two adjacent R⁶ groups or two adjacent R⁷ groups are incorporated into a C3-C7 aliphatic ring or an aromatic ring, and wherein R⁶ and R⁷ are the same or different;

R⁸ and R⁹ are independently H, halogen, C1-C8 alkyl, C1-C8 alkoxy, phenyl, substituted phenyl, 1-naphthyl, 2-naphthyl, heteroaryl, or benzyl, and wherein a substituent on said substituted phenyl is halogen, C1-C8 alkyl, alkoxy, with a substituent number of 1-5, and said heteroaryl is furyl, thienyl, or pyridyl, and m=0-3; or when m≥2, adjacent R⁹ groups, or R⁸ and R⁹ groups, are incorporated into a C3-C7 aliphatic ring or an aromatic ring, and wherein R⁸ and R⁹ are the same or different; and R¹⁰ is H, C1-C8 alkyl, phenyl, substituted phenyl, 1-naphthyl, 2-naphthyl, heteroaryl, or benzyl, and wherein a substituent on said substituted phenyl is $C_1$-$C_8$ alkyl or alkoxy, with a substituent number of 1-5, and said heteroaryl is furyl, thienyl, or pyridyl.

5. The method for kinetic resolution of racemic δ-hydroxyl esters via asymmetric catalytic hydrogenation according to claim 1, wherein said chiral spiro pyridyl amido phosphine ligand Iridium complex catalyst comprises one selected from the following structures:

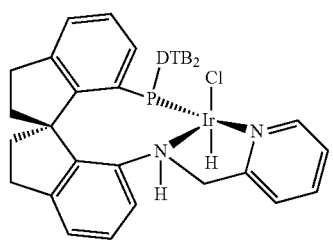

IIIa

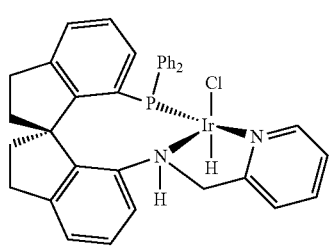

IIIb

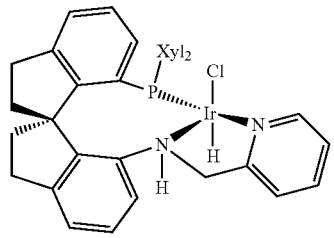

IIIc

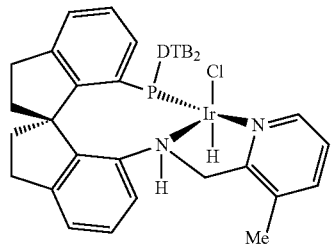

IIId

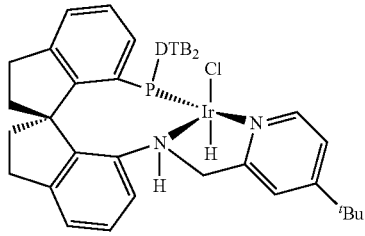

IIIe

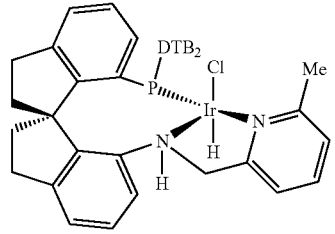

IIIf

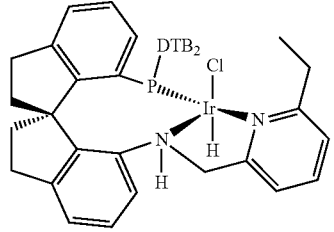

IIIg

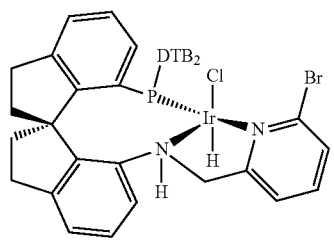

IIIh

-continued

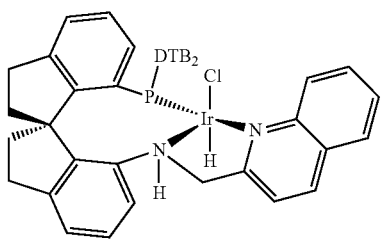

IIIi

Wherein, wherein DTB is 3,5-di-tert butyl phenyl, Xyl is 3,5-di-methyl phenyl, $^t$Bu is tert-butyl; and wherein the Iridium catalyst is in an (R)-configuration or in an (S)-configuration.

6. The method for kinetic resolution of racemic δ-hydroxyl esters via asymmetric catalytic hydrogenation according to claim 2, wherein the racemic δ-hydroxyl esters, the catalyst, and the base are added to the solvent and a resulting reaction mixture is stirred for 0.5-24 h to react under a hydrogen atmosphere of 1-100 atm to produce the chiral δ-hydroxyl ester and the corresponding chiral 1,5-diols.

7. The method for kinetic resolution of racemic δ-hydroxyl esters via asymmetric catalytic hydrogenation according to claim 1, wherein the base is potassium tert-butoxide, sodium tert-butoxide, potassium isopropoxide, sodium isopropoxide, potassium hydroxide, sodium hydroxide, potassium carbonate, or sodium carbonate.

8. The method for kinetic resolution of racemic δ-hydroxyl esters via asymmetric catalytic hydrogenation according to claim 2, wherein the solvent is selected from any single or mixture of an alcohol solvent, an ether solvent, or an arene solvent; wherein the alcohol solvent is methanol, ethanol, propanol, isopropanol, or butanol; wherein the ether solvent is THF, methyl tert-butyl ether, or dioxane; wherein the arene solvent is toluene, DMF, or DMSO.

9. The method for kinetic resolution of racemic δ-hydroxyl esters via asymmetric catalytic hydrogenation according to claim 1, further comprising using the produced chiral active δ-hydroxyl ester as a chiral starting material in an asymmetric synthesis of a chiral drug selected from the group consisting of (R)-lisofylline, (+)-civet, (−)-indolizidine 167B, and (−)-coniine.

10. The method for kinetic resolution of racemic δ-hydroxyl esters via asymmetric catalytic hydrogenation according to claim 2, wherein said chiral spiro pyridyl amido phosphine ligand Iridium complex catalyst comprises one selected from the following structures:

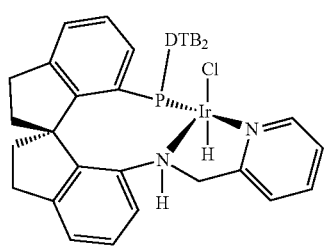

IIIa

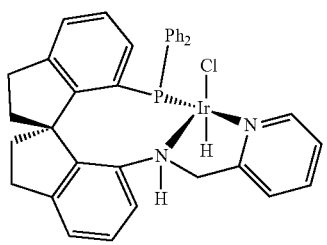

IIIb

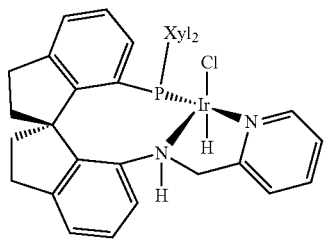

IIIc

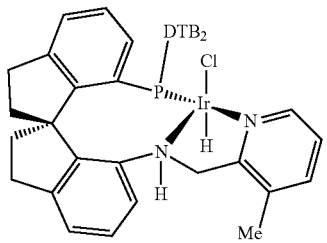

IIId

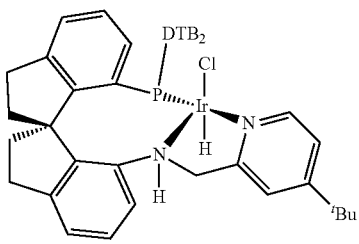

IIIe

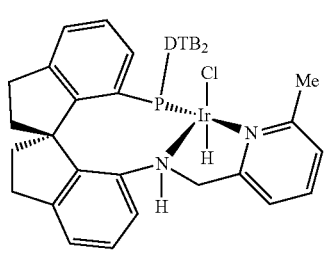

IIIf

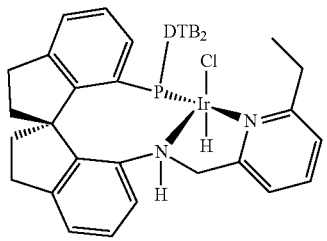

IIIg

-continued

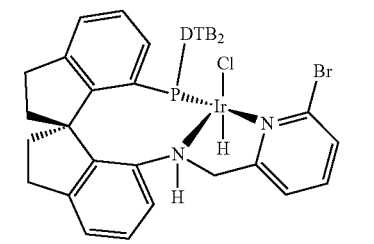

IIIh

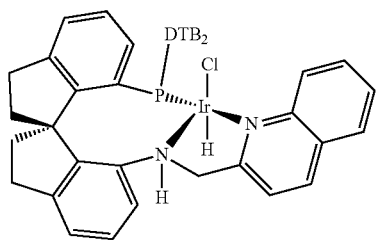

IIIi wherein DTB is 3,5-di-tert butyl phenyl, Xyl is 3,5-dimethyl phenyl, $^t$Bu is tert-butyl; and wherein the Iridium catalyst is in an (R)-configuration or in an (S)-configuration.

11. The method for kinetic resolution of racemic δ-hydroxyl esters via asymmetric catalytic hydrogenation according to claim 2, wherein the base is potassium tert-butoxide, sodium tert-butoxide, potassium isopropoxide, sodium isopropoxide, potassium hydroxide, sodium hydroxide, potassium carbonate, or sodium carbonate.

* * * * *